United States Patent [19]

Malvern, deceased

[11] Patent Number: Plant 6,371

[45] Date of Patent: Nov. 1, 1988

[54] CHRYSANTHEMUM PLANT NAMED MALVERN'S DIGNITY

[75] Inventor: Richard W. Malvern, deceased, late of Manchester, Mo., by Keith M. Malvern, administrator

[73] Assignee: Ball Pan Am Plant Company, Parrish, Fla.

[21] Appl. No.: 17,171

[22] Filed: Feb. 20, 1987

Related U.S. Application Data

[63] Continuation of Ser. No. 815,170, Dec. 31, 1985, abandoned.

[51] Int. Cl.[4] ..... A01H 5/00

[52] U.S. Cl. ..... Plt./77

*Primary Examiner*—Robert E. Bagwill

*Attorney, Agent, or Firm*—Schwartz, Jeffery, Schwaab, Mack, Blumenthal & Evans

[57] ABSTRACT

A chrysanthemum plant named Malvern's Dignity having standard form, white ray floret color, and high degree of incurving of the ray florets.

1 Drawing Sheet

This is a continuation of application Ser. No. 815,170, filed Dec. 31, 1985 now abandoned.

The present invention comprises a new and distinct cultivar of *Dentrenthema morifolium,* Ramat., previously *Chrysanthemum morifolium,* Ramat., hereinafter referred to by the cultivar name Malvern's Dignity.

Malvern's Dignity was discovered as a spontaneous mutation among plants of the variety Hartmann's Dignity grown in a cultivated area.

Malvern's Dignity was discovered by Richard W. Malvern at the greenhouses of Richard Malvern Florist, Inc., Manchester, Mo, in May of 1980.

The first act of asexual reproduction of Malvern's Dignity was accomplished when vegetative cuttings were taken from the selection in August of 1980 in a controlled environment in Manchester, Mo. by a technician working under formulations established and supervised by Richard W. Malvern. Horticultural examination of selected units initiated in August of 1980 has demonstrated that the combination of characteristics as herein disclosed for Malvern's Dignity are firmly fixed and are retained through successive generations of asexual reproduction.

Malvern's Dignity has not been observed under all possible environmental conditions. The phenotype may vary significantly with variations in environment such as temperature, light intensity and day length. The following observations, measurements and comparisons describe plants grown in Parrish, Fla. under greenhouse conditions which approximate those generally used in commercial practice.

The following traits have been repeatedly observed and are determined to be basic characteristics of Malvern's Dignity which in combination distinguish this chrysanthemum as a new and distinct cultivar:

1. The incurving of the new cultivar is substantially more pronounced than in the parent Hartmann's Dignity.

2. The petal count of Malvern's Dignity is lower than in the parent.

3. The white flower color is less intense than in Hartmann's Dignity, being more similar to the ray floret color of Nob Hill, a well known commercial variety.

4. Malvern's Dignity has a slightly smaller diameter than Hartmann's Dignity, and has a 3–4 days earlier response.

Of the many commercial cultivars known to the present inventor, the most similar in comparison to Malvern's Dignity is the parent Hartmann's Dignity and Malvern's Yellow Dignity, a spontaneous yellow mutation of the new cultivar disclosed in a pending application of applicant. The difference between Malvern's Dignity and its parent are noted above, other characteristics being the same or similar. The new cultivar is distinguished from Malvern's Yellow Dignity primarily by the difference in ray floret color.

The accompanying photographic drawing shows typical inflorescence and foliage characteristics of Malvern's Dignity and Malvern's Yellow Dignity. The black and white photograph shows Malvern's Dignity on the left and Malvern's Yellow Dignity on the right, with the florets of Malvern's Yellow Dignity being colored to depict true flower color.

In the following description, color references are made to The Royal Horticultural Society Colour Chart (R.H.S.). The color values were determined between 10:00 a.m. and 12:00 noon on Mar. 25, 1985 under fluorescent lights at Bradenton, Fla.

Classification:

*Botanical.*—*Dentrenthema morifolium,* Ramat., cv Malvern's Diginty.

*Commercial.*—Standard cut.

INFLORESCENCE

A. Capitulum:

*Form.*—Incurved.

*Type.*—Formal.

*Diameter across face.*—12–15 cm.

B. Corolla of ray florets:

*Color (general tonality from a distance of three meters).*—White.

*Color (upper surface).*—Outer florets, upper and reverse sides white RHS 155B at all seasons.

*Color (under surface).*—Inside florets, upper and reverse sides yellow RHS 2D at all seasons.

C. Corolla of disc florets: Insignificant.

D. Reproductive organs:

*Androecium.*—Present in disc florets only; insignificant.

*Gynoecium.*—Present in ray florets only; insignificant.

PLANT

A. General appearance:

*Height.*—2–6 meters, depending on culture.

B. Foliage:

*Color (upper surface).*—RHS 147A.

*Color (under surface).*—RHS 147B.

*Shape.*—Deeply lobed and slightly serrated.

I claim:

1. A new and distinct cultivar of chrysanthemum plant named Malvern's Dignity, as described and illustrated, and particularly characterized by its standard form, white ray floret color, and a high degree of incurving of the ray florets.

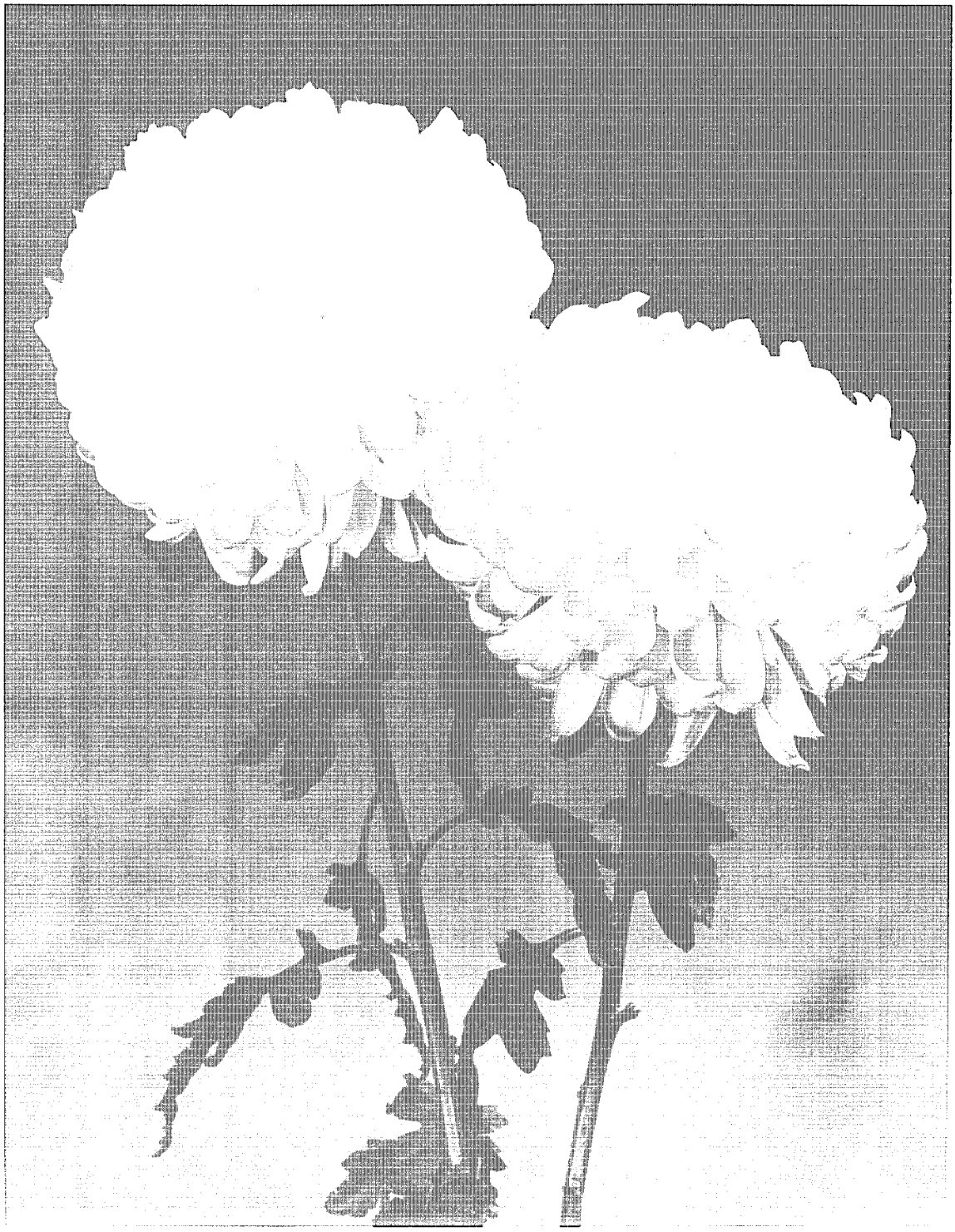

* * * * *